US012156867B2

(12) United States Patent
Bocci et al.

(10) Patent No.: US 12,156,867 B2
(45) Date of Patent: Dec. 3, 2024

(54) MELANOCORTIN AGENTS FOR USE IN THE THERAPEUTIC TREATMENT OF MELANOMA, TUMORS OF THE GASTROINTESTINAL TRACT, AND THYROID CARCINOMA

(71) Applicants: UNIVERSITA' DI PISA, Pisa (IT); UNIVERSITA' DEGLI STUDI DI MODENA E REGGIO EMILIA, Modena (IT)

(72) Inventors: Guido Bocci, Pisa (IT); Teresa Di Desidero, Pisa (IT); Daniela Giuliani, Modena (IT); Salvatore Guarini, Modena (IT); Paola Orlandi, Pisa (IT); Alessandra Ottani, Modena (IT); Carla Maria Francesca Pardini, Pisa (IT); Francesca Vaglini, Pisa (IT)

(73) Assignees: UNIVERSITA' DI PISA, Pisa (IT); UNIVERSITA' DEGLI STUDI DI MODENA E REGGIO EMILIA, Modena (IT)

( * ) Notice: Subject to any disclaimer, the term of this patent is extended or adjusted under 35 U.S.C. 154(b) by 1020 days.

(21) Appl. No.: 17/253,883

(22) PCT Filed: Jun. 14, 2019

(86) PCT No.: PCT/IB2019/054992
§ 371 (c)(1),
(2) Date: Dec. 18, 2020

(87) PCT Pub. No.: WO2019/243974
PCT Pub. Date: Dec. 26, 2019

(65) Prior Publication Data
US 2021/0260037 A1   Aug. 26, 2021

(30) Foreign Application Priority Data
Jun. 18, 2018 (IT) .................. 102018000006399

(51) Int. Cl.
*A61K 31/4164* (2006.01)
*A61K 31/437* (2006.01)
*A61K 45/06* (2006.01)
*A61P 35/00* (2006.01)

(52) U.S. Cl.
CPC ........ *A61K 31/4164* (2013.01); *A61K 31/437* (2013.01); *A61K 45/06* (2013.01); *A61P 35/00* (2018.01)

(58) Field of Classification Search
CPC .............. A61K 31/4164; A61K 31/437; A61K 45/06; A61K 2300/00; A61P 35/00
See application file for complete search history.

(56) References Cited

U.S. PATENT DOCUMENTS

2002/0004485 A1   1/2002   Wei et al.

FOREIGN PATENT DOCUMENTS

WO        9943709 A2    9/1999

OTHER PUBLICATIONS

International Search Report and Written Opinion for International Patent Application No. PCT/IB2019/054992, mailed Sep. 26, 2019, 10 pages.
Vos T. J. et al., Identification of 2-{2-[2-(5-Bromo-2-methoxyphenyl)-ethyl]-3-fluoro-phenyl}-4,5-dihydro-1H-imidazole (ML00253764), a Small Molecule Melanocortin 4 Receptor Antagonist That Effectively Reduces Tumor Induced Weight Loss in a Mouse Model, Journal Of Medicinal Chemistry, Mar. 1, 2004, pp. 1602-1604, vol. 47, Issue 7, American Chemical Society, USA.
J. R. Nicholson et al., Peripheral Administration of a Melanocortin 4-Receptor Inverse Agonist Prevents Loss of Lean Body Mass in Tumor-Bearing Mice, The Journal Of Pharmacology And Experimental Therapeutics, May 1, 2006, pp. 771-777, vol. 317, Issue 2, The American Society of Pharmacology And Experimental Therapeutics, USA.
Vaglini Francesca et al., Melanocortin Receptor-4 and Glioblastoma Cells: Effects of the Selective Antagonist ML00253764 Alone and in Combination with Temozolomide In Vitro and In Vivo, Molecular Neurobiology, Aug. 8, 2017, pp. 4984-4997, vol. 55, No. 6, Springer Science+Business Media, USA.

*Primary Examiner* — Sun Jae Yoo
(74) *Attorney, Agent, or Firm* — Armstrong Teasdale LLP

(57) ABSTRACT

A method of therapeutic treatment of a tumor pathology including melanoma, tumors of the gastrointestinal tract, and/or thyroid carcinoma by administering to a subject in need thereof melanocortin receptor-4 (MC4R) antagonists is provided. The melanocortin receptor-4 antagonists are suitable in a targeted anti-tumor treatment, and particularly in an adjuvant therapy or in a therapy affecting onset and/or progression of tumor metastasis. A pharmaceutical composition including a melanocortin receptor-4 (MC4R) antagonist in a pharmaceutically acceptable vehicle, and in combination with optional adjuvants, stabilizers and/or preservatives, is also provided.

12 Claims, 9 Drawing Sheets

(A)

(B)

(A)

(B)

(A) (B)

* $P<0.05$ vs HUVEC; n= 8-12 repeats (A)

(B)

(A)

(B)

(A)

(B)

(C)

(A)

(B)

(A)

(B)

MELANOCORTIN AGENTS FOR USE IN THE THERAPEUTIC TREATMENT OF MELANOMA, TUMORS OF THE GASTROINTESTINAL TRACT, AND THYROID CARCINOMA

CROSS-REFERENCE TO RELATED APPLICATIONS

This application is a National Stage Application of International Patent Application No. PCT/IB2019/054992, having an International Filing Date of Jun. 14, 2019, which claims the benefit of priority to Italian Patent Application No. 102018000006399, filed Jun. 18, 2018, the entire contents of which are hereby incorporated by reference herein.

The present invention falls within the field of therapeutic treatments of tumor pathologies, particularly solid tumors, more particularly melanoma, tumors of the gastrointestinal tract, and thyroid carcinoma.

FIELD OF THE INVENTION

Despite the significant progress achieved in recent years by surgical therapy, which represents the preferred intervention for this type of tumors in the early stage, the incidence of mortality due to melanoma, gastrointestinal tumors and thyroid carcinoma remains high.

BACKGROUND OF THE INVENTION

Melanoma is a cutaneous malignant neoplasm that originates from melanocytes, i.e. skin cells located at the level of the epidermis. The incidence of this neoplasm is constantly increasing, although its frequency is significantly lower than basal cell and spinocellular carcinomas. Melanoma can occur in any body district, on healthy skin or on a congenital or acquired melanocytic nevus. More rarely, it occurs in different sites, such as the eye (the conjunctiva or choroid), the vulva, the anus, the oral or nasal cavity. In a non-negligible percentage of cases the diagnosis is made following the appearance of lymph node or visceral metastases with no clinical evidence of the primitive melanoma ("unknown primitive melanoma"). In recent years, significant progress in the biomolecular field has led to the identification of specific mutations in the melanocyte cell. 50-60% of melanomas exhibit BRAF mutations, which is a gene coding for a protein kinase involved in cell growth regulation. NRAS mutation is found in 15-30% of melanomas and is mutually exclusive with BRAF mutation; p16 and p14ARF (CDKN2A) are often inactivated in melanomas that occur on chronically photoexposed skin, while cKIT mutations are found in acral/mucosal melanomas and on photodamaged skin.

According to the Surveillance, Epidemiology and End Results (SEER) Program of the National Cancer Institute, the incidence of melanoma in the US was estimated at 6.8 per 100,000 person-year in 1973, while in 2005 this incidence increased to 20.8. However, there are many variations in incidence in the different ethnic groups and geographical areas. The trend is constantly increasing in Italy too, with a tendency to a doubling of melanoma diagnoses in 10 years. In Northern Europe and the US, excluding skin cancers, this tumor accounts for 2-3% of all malignant tumors. In Europe the frequency of melanoma is 1% of all male tumors and 1.8% of all female tumors. The country with the highest incidence of melanoma in the world is Australia (55.8 cases per 100,000 inhabitants in men and 41.1 in women), followed by New Zealand and Northern Europe, whereas the incidence of the tumor is lower in Japan and Central Africa (0.4/100,000 inhabitants). In Italy, incidence rates range from 6 cases per 100,000 in the south to 15 cases per 100,000 in the northern regions. There are differences among the various regions: the highest rates, between 12.5 and 13, are recorded in Friuli Venezia Giulia, Romagna, Marche, Trentino and Tuscany (AIRTUM, Associazione Italiana Registri Tumori). The median age at diagnosis is approximately 50 years, earlier than that of other cutaneous epithelial neoplasms.

Among the solid tumors characterized by a marked aggressiveness are also gastrointestinal tumors, including colorectal carcinomas, pancreatic carcinoma, gastric carcinoma, esophagus cancer, and biliary tract cancer. The overall incidence of gastrointestinal malignancies appears to be increasing, and supporting these data, gastric cancer is reported in Europe as the fourth leading cause of death from cancer and the second in the world. Thyroid carcinoma also exhibits a significant trend in the increase in the number of cases, for example, being the fifth most frequent tumor in the United States.

The clinical relevance of the aforementioned tumor pathologies-melanoma, tumors of the gastrointestinal tract and thyroid carcinoma—is also increased both by the high metastatic potential they have, with appearance of metastases in 15-35% of patients, and the high capacity of locoregional infiltration. In addition, patients suffering from these advanced-stage tumors generally experience the onset of the "neoplastic cachexia" pathological condition, a complex metabolic syndrome characterized by weight loss and muscular atrophy.

Currently, the treatment of choice for these neoplasms diagnosed in the early stage remains surgery, and drug therapy is generally implemented after the intervention as an adjuvant therapy or in the presence of metastatic disease. The only drug for which a potential efficacy has so far been documented in the adjuvant treatment of melanoma is interferon-alpha (IFN). Studies published in the literature have used schedules with different doses of IFN, but the most effective doses and administration modes have not been uniquely defined yet. Cutaneous or subcutaneous involvement is a frequent event in the clinical course of melanoma: skin lesions are present in 10-17% of patients and in almost 50% of patients with metastatic disease. The choice of the treatment method for skin metastases depends on the location and number of lesions, the systemic involvement, the age and general condition of the patients. Surgery is the most appropriate treatment when the lesions are clustered in a limited area. For diffuse metastases in a limb, hyperthermic perfusion with antiblastic drugs can be considered, whereas radiation therapy can only be used for palliative purposes. The prognosis for advanced metastatic melanoma is poor. However, the introduction in the therapeutic field of new drugs—both the so-called "check-points inhibitors" and the targeted molecular therapies—have brought about a radical change in the management of these patients with a significant improvement in mean survival. The first anti-BRAF drug that showed a significant impact on the clinical course in patients with advanced metastatic melanoma was Vemurafenib, followed by Dabrafenib. These tumor growth inhibitor drugs were associated with a response rate of around 50% and a remarkable response-inducing rate, with a median of just over 1 month. However, a large percentage of patients undergo disease progression due to mechanisms of escape from BRAF inhibition, in most cases following MAP kinase pathway activation downstream of BRAF. In three randomized trials, the combined administration of anti-MEK and anti-BRAF compounds was in fact associated with a significant greater clinical efficacy compared to monotherapy, in terms of response rates (up to 68% for the "combo target"), progression-free survival and overall survival. Furthermore, the "combo target" also has a significantly better toxicity profile than monotherapy. Recently, antibody-based therapy has also been applied to combat melanoma. In particular, antibodies that bind to CTLA-4, a surface molecule on helper T cells, or to the PD-1 protein, have shown activity by inducing an active immune response against tumor cells. Randomized studies have shown that using the ipilimumab antibody allows a significant increase in survival compared to standard chemotherapy in patients with advanced metastatic melanoma.

The most commonly used chemotherapy regimens in the treatment of tumors of the gastrointestinal tract are usually combinations of multiple drugs to allow extension of overall survival. Said regimens substantially provide the use of antimetabolite chemotherapeutics (e.g. 5-fluorouracil and derivatives thereof or gemcitabine) in association with camptothecins (e.g. Irinotecan) or platinum compounds (e.g. oxaliplatin). Anti-EGFR monoclonal antibodies or anti-angiogenic drugs, such as for example bevacizumab, ramucirumab and regorafenib, are also used.

With regard to thyroid carcinoma therapy, ablation of the thyroid residue by iodine-131 is generally recommended following thyroidectomy. The purpose of the radiometabolic therapy with iodine 131 is to destroy the normal thyroid tissue, which almost always remains even after total thyroidectomy, and eliminate any neoplastic microfoci inside the thyroid residues or in other sites. Finally, radiation therapy, chemotherapy and tyrosine kinase inhibitors are recommended in the case of highly aggressive and inoperable tumors or those characterized by de-differentiation, although with extremely limited efficacy results.

Melanocortins are peptide hormones derived from proteolytic cleavage of proopiomelanocortin (POMC) and include α-, β-, γ-MSH (melanocyte stimulating hormone) and adrenocorticotropin (ACTH). These hormones are present in serum and many tissues, such as the central nervous system (CNS) and the skin, and have a wide range of effects mediated by five different G protein-coupled transmembrane receptor subtypes. Receptor 1 (MC1R) is mainly expressed in melanocytes and mediates the effects on skin and hair pigmentation, whereas receptor 2 (MC2R) is mainly expressed in the adrenal cortex, where it mediates the effects of ACTH on glucocorticoid synthesis and release. The main sites of expression of receptor 5 (MC5R) are the exocrine glands and skeletal muscle. As for the expression of receptors 3 and 4 (MC3R, MC4R), it is mainly, but not exclusively, located in the central nervous system. In particular, the MC4R receptor is widely distributed in the brain areas of the hypothalamus, thalamus and cortex, with a particularly high concentration in the paraventricular nucleus and the lateral hypothalamic area, which are regions that play a key role in regulating the energy balance. Indeed, studies conducted on murine models have shown that MC4R receptors are involved in feeding behaviour, metabolism regulation, sexual behaviour, and male erectile function. MC4R gene mutations have been reported as associated with human hereditary obesity, with a prevalence of 1.0-2.5% in individuals with body mass indexes above 30, thus making it the most common, known genetic defect predisposing to obesity. Pharmacological modulation of the activity of this receptor therefore represents a therapeutic approach of great interest in the field of metabolic diseases. In particular, a small molecule that acts as a selective non-peptide antagonist of MC4R has been synthesized and used experimentally to counteract the weight loss that occurs in patients suffering from sarcopenia and neoplastic cachexia (Vos T J et al.; Identification of 2-[2-[2-(5-bromo-2-methoxyphenyl)-ethyl]-3-fluorophenyl]-4,5-dihydro-1H-imidazole, a small molecule melanocortin 4 receptor antagonist that effectively reduces tumor-induced weight loss in a mouse model. J Med Chem. 2004; 47:1602-1604). Recent studies have also shown that MC4R stimulation with agonists causes a major cytoprotective action in different tissues under hypoxic conditions, such as myocardial ischemia, stroke, head injury and haemorrhagic shock, as well as the ability of inducing neurogenesis (development of new functioning neurons), by stimulating cell proliferation activity. The scientific paper by Vaglini F et al. (Melanocortin Receptor-4 and Glioblastoma Cells: Effects of the Selective Antagonist ML00253764 Alone and in Combination with Temozolomide In Vitro and In Vivo. Mol Neurobiol. 2018; 55:4984-4997) described for the first time the presence of the functionally active MC4R receptor in glioblastoma tumor cells, as well as the anti-tumor effect in this particular cell type mediated by the inhibition of this receptor through the use of selective antagonists.

Patent application US 2002/0004485 describes the action of peptide antagonists of melanocortin receptors on pigmentation in melanophores of *Xenopus laevis* larvae and in mammalian cells stably transfected with DNA encoding the aforementioned receptors. This patent application mentions the use of melanocortin antagonists for the therapeutic treatment of melanoma in a totally speculative manner. However, no support or experimental evidence is provided in this regard.

In this context, therefore, the dramatic need arises for the development of therapeutic strategies aimed at eradicating aggressive tumor diseases such as melanoma, tumors of the gastrointestinal tract and thyroid carcinoma, by contrasting their onset and progression, which are suitable for obtaining a lasting clinical response as well as preventing tumor recurrence.

SUMMARY OF THE INVENTION

Therefore, the object of the present invention is to provide a medicament capable of contrasting with high efficacy the growth and proliferation of melanoma, tumors of the gastrointestinal tract and thyroid carcinoma, while reducing possible adverse effects to a minimum extent.

Another object is to provide a medicament which is active as an adjuvant in cancer therapeutic treatment and at the same time effective in preventing and inhibiting the onset of metastases of these neoplasms.

A further object is to provide a medicament which, in addition to the aforementioned anti-tumor activity, is effective in controlling the neoplastic cachexia pathological condition typically associated with the advanced stages of melanoma, tumors of the gastrointestinal tract and thyroid carcinoma.

These and other objects are achieved by a melanocortin receptor-4 antagonist for use in the therapeutic treatment of a tumor pathology selected from the group consisting of melanoma, tumors of the gastrointestinal tract and thyroid carcinoma, as described and claimed herein.

Preferred embodiments of the invention are also described.

As will be explained in more detail in the following experimental section, the present inventors have shown for the first time the presence of the melanocortin receptor 4 (MC4R) and its functional activity in cells isolated from some types of human solid tumors, more particularly in cells isolated from melanoma, tumors of the gastrointestinal tract and thyroid carcinoma; as well as a significant increase in the expression of this melanocortin receptor in the aforementioned tumor cells compared to normal endothelial control cells.

Based on these findings, the present inventors investigated the role of the melanocortin receptor 4 as a potential molecular target for therapies aimed at counteracting the proliferation and survival cell processes that promote and sustain the onset and/or progression of such neoplastic diseases as melanoma, tumors of the gastrointestinal tract and thyroid carcinoma. In order to determine the possible effects of receptor modulation on the aforementioned tumor cells, in vitro cellular assays were conducted by using MC4R antagonists already known in the prior art, which, as shown in FIGS. 6, 8 and 10, not only revealed marked anti-proliferative and pro-apoptotic actions by treatment with the antagonist compound, but also allowed surprisingly significant levels of such anti-tumor activities to be recorded compared to control samples.

Therefore, a new therapeutic agent for the treatment of melanoma, tumors of the gastrointestinal tract and thyroid carcinoma is the melanocortin receptor-4 antagonist shown by the general formula (I) below:

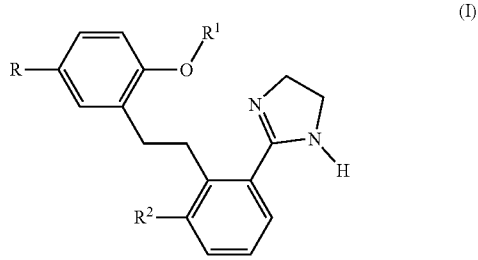

(I)

or pharmaceutically acceptable salts and esters thereof, wherein

R and $R^2$ are a halogen atom; and $R^1$ is a $C_1$-$C_4$ alkyl group.

The halogen atom is selected from the group consisting of fluorine (F), iodine (I), chlorine (Cl) and bromine (Br). The halogen atom preferably is fluorine or bromine.

A $C_1$-$C_4$ alkyl group is selected from the group consisting of methyl, ethyl, n-propyl, isopropyl, n-butyl, isobutyl, sec-butyl and tert-butyl.

In a preferred embodiment, R is a bromine atom and/or $R^2$ is a fluorine atom.

According to another preferred embodiment, $R^1$ is a methyl group.

In a more preferred embodiment, the melanocortin receptor-4 antagonist for use according to the invention has the formula (II)

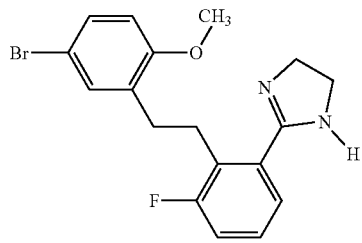

(II)

Within the scope of the present description, the melanocortin receptor-4 antagonist for use according to the invention and shown by formula (II) is also referred to as ML00253764.

The therapeutic approach based on the administration of the melanocortin receptor-4 antagonist for use according to the invention has the undeniable advantage of allowing an anti-tumor treatment targeted to a molecular target since it is aimed solely at modulating MC4R receptor activity. The resulting high therapeutic specificity therefore entails a significant reduction in the extent of the adverse effects, which are instead typical of the non-targeted chemotherapy and often difficult to manage by patients, and in some cases so severe as to compromise the ambition to a satisfying quality of life.

In the context of the present invention, the melanocortin receptor-4 antagonist for use according to the invention can be administered to a cancer patient as an adjuvant therapy, that is to say as a treatment that is performed after the primary therapeutic act, for example after surgical resection of the tumor mass, in order to reduce the risk of local and systemic disease relapse with the formation of micro metastases and thereby increase the chances of a full recovery.

Additionally, or alternatively, the anti-tumor therapy based on the melanocortin receptor-4 antagonist for use according to the invention can be designed to contrast local recurrence and metastasis spread, which are frequently associated with the aggressive forms of such diseases as melanoma, tumors of the gastrointestinal tract and thyroid carcinoma. It is worthy to mention that the small size of the melanocortin receptor-4 antagonist for use according to the invention makes this molecule particularly suitable for tissue penetration, for example into the central nervous system tissues, allowing its anti-tumor therapeutic activity to be performed, for example, against brain metastases, which are currently without cure.

Therefore, according to a preferred embodiment, the melanocortin receptor-4 antagonist for use according to the invention is used in an adjuvant therapy or a therapy which affects metastasis onset and/or progression.

In another preferred embodiment, the melanocortin receptor-4 antagonist for use according to the invention is suitable, together with the anti-tumor therapeutic activity, for controlling neoplastic cachexia.

According to this preferred embodiment, in addition to the significant therapeutic efficacy detected for the first time by the present inventors in counteracting the onset and/or progression of such diseases as melanoma, tumors of the gastrointestinal tract and thyroid carcinoma, treatment with the melanocortin receptor-4 antagonist for use according to the invention advantageously allows the anti-tumor treatment and the control of the serious metabolic disorders typical of these neoplasms, generally in the most advanced stages of the disease, to be combined in a single therapeutic act.

In a further embodiment, the therapeutic treatment with the melanocortin receptor-4 antagonist for use according to the invention also comprises administering one or more cytostatic and/or cytotoxic agents. Suitable cytostatic and/or cytotoxic agents include alkylating drugs, anti-metabolite drugs, topoisomerase inhibiting drugs, anti-microtubule drugs, anti-hormone drugs, anti-angiogenic drugs, immunotherapy drugs, cytotoxic monoclonal antibodies, protein kinase inhibitors such as, for example, BRAF inhibitors, including for example Vemurafenib and Dabrafenib, MEK inhibitors, including for example Trametinib and Cobimetinib, and tyrosine kinase inhibitors, and any combination thereof. The administration of the MC4R antagonist for use according to the invention in combination with BRAF inhibitors, preferably Vemurafenib, is highly preferred since said combination, as shown in FIG. 9, produces a marked synergistic antineoplastic effect.

A further object of the present invention is a pharmaceutical composition comprising a melanocortin receptor-4 antagonist as defined in appended claim 1 for use in the therapeutic treatment, in a patient in need thereof, of a tumor pathology selected from the group consisting of melanoma, tumors of the gastrointestinal tract and carcinoma thyroid, in combination with pharmaceutically acceptable vehicles, excipients and/or diluents.

The pharmaceutical composition of the present invention can be formulated into any suitable dosage form, for example for administration via the enteral (oral or gastroenteral, rectal, sublingual, buccal), parenteral (inhalation, ocular, intravenous, intraarterial, transcutaneous, intramuscular, intradermal, intranasal, subcutaneous, intraperitoneal, intrathecal, intracerebral, intracerebroventricular, hyperthermic isolated limb perfusion) and topical routes (direct contact of the drug with the site of action and/or the skin and/or the mucous membranes and/or the ocular surface). For example, the pharmaceutical composition for use according to the invention can be in a formulation suitable for treatment of cutaneous melanoma metastases. Of course, the selection of suitable vehicles, excipients and/or diluents is carried out depending on the desired form of administration and this selection is within the skills of those of ordinary skill in the art. The selection of the dose of active principle and the dosage regimen also fall within the skills of those of ordinary skill in the art, and their selection depends on several factors, such as for example the age of the patient and the degree of progression of the disease.

In a preferred embodiment, the therapeutic regimen is based on administering to the patient the pharmaceutical composition comprising the MC4R antagonist for use according to the invention preferably at a daily dose comprised between 1 and 100 mg/kg body weight of the patient, preferably a daily dose of at least 50 mg/kg body weight of the patient, more preferably a daily dose of at least 25 mg/kg body weight of the patient.

According to this embodiment, the pharmaceutical composition for use according to the invention can be administered through a continuous regimen, for example by continuous infusion, or alternatively as a single dose, one or more times a day. Said single-dose regimen is advantageously allowed by the longer plasma half-life, more specifically hours vs. minutes, of the melanocortin receptor-4 antagonist molecule compared, for example, to target molecular peptide drugs which are subject to the degradation action of blood peptidases.

BRIEF DESCRIPTION OF THE FIGURES

The experimental section that follows is provided for illustration purposes only and does not limit the scope of the invention as defined in the appended claims. In the experimental section, reference is made to the accompanying drawings, wherein:

Figure 6:
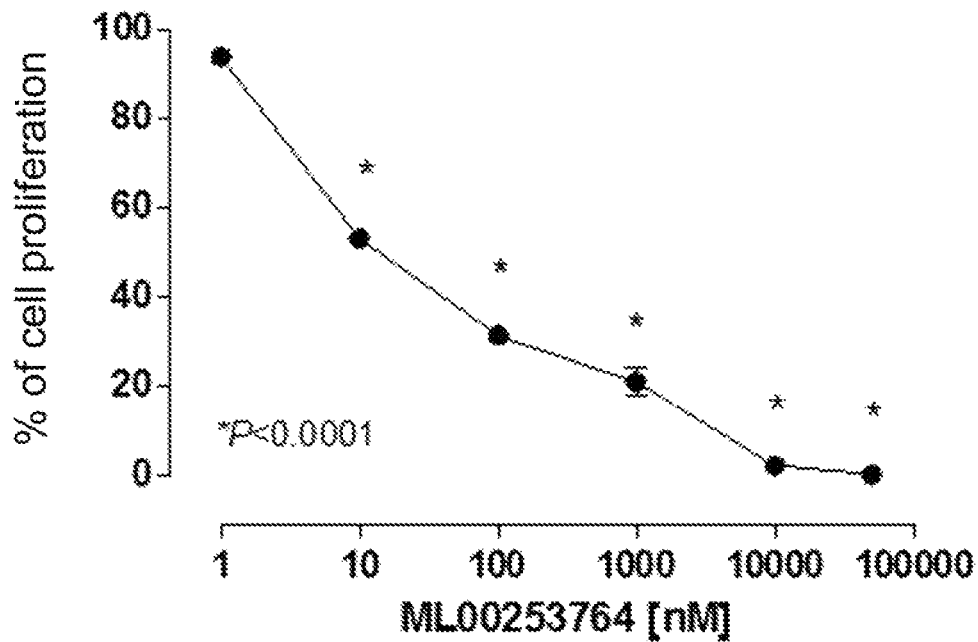
Figure 6:
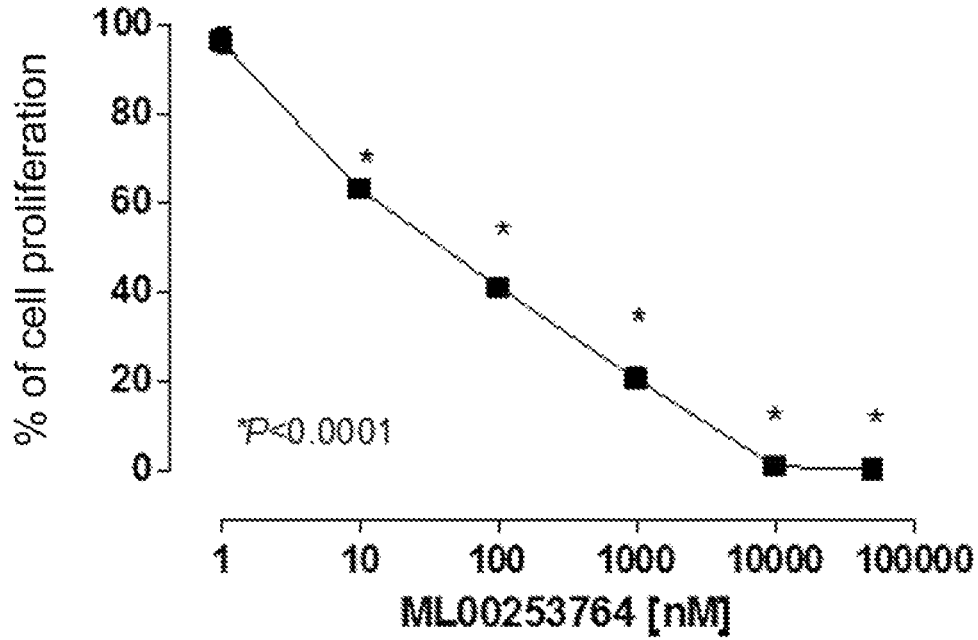

The graphs in FIG. 6 illustrate the in vitro anti-proliferative effect of the melanocortin receptor-4 antagonist ML00253764 on A-2058 (A) and WM 266-4 (B) human melanoma cell lines. Anti-proliferative effects were studied after 72 hours of drug exposure. The data are presented as mean percentage values (±S.E.M.) of cell proliferation in controls treated with the vehicle alone. *$P<0,0001$ vs. controls. All experiments were repeated, independently, three times with at least three samples for each concentration.

Figure 7:
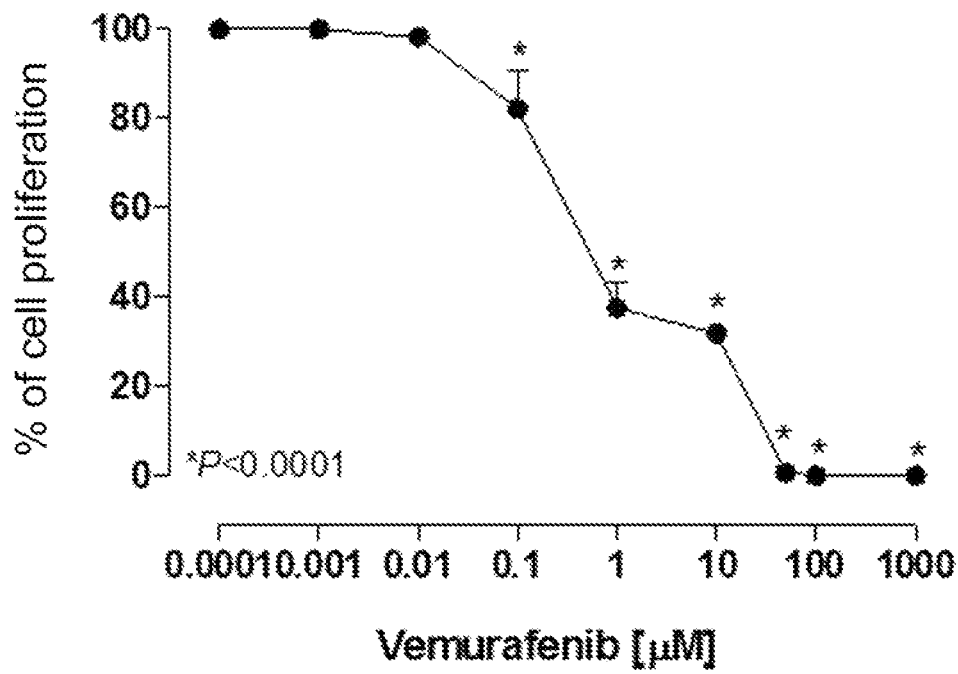
Figure 7:
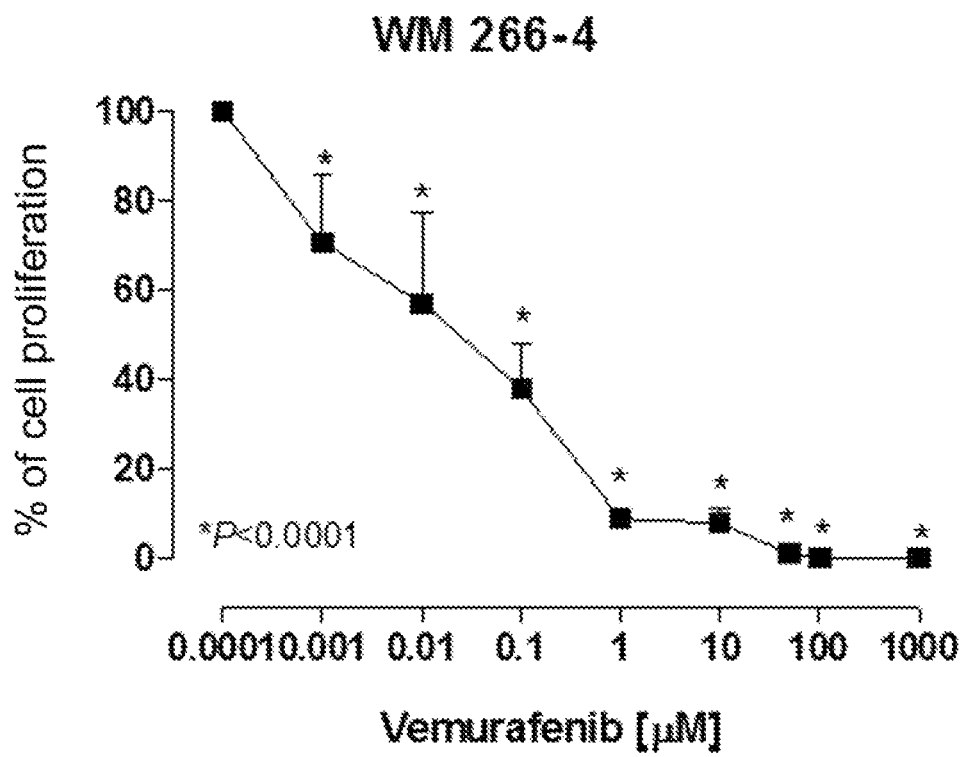

The graphs in FIG. 7 illustrate the in vitro anti-proliferative effect of the compound Vemurafenib on A-2058 (A) and WM 266-4 (B) human melanoma cell lines. Anti-proliferative effects were studied after 72 hours of drug exposure. The data are presented as mean percentage values (±S.E.M.) of cell proliferation in controls treated with the vehicle alone. *$P<0,0001$ vs. controls. All experiments were repeated, independently, three times with at least three samples for each concentration.

Figure 8:
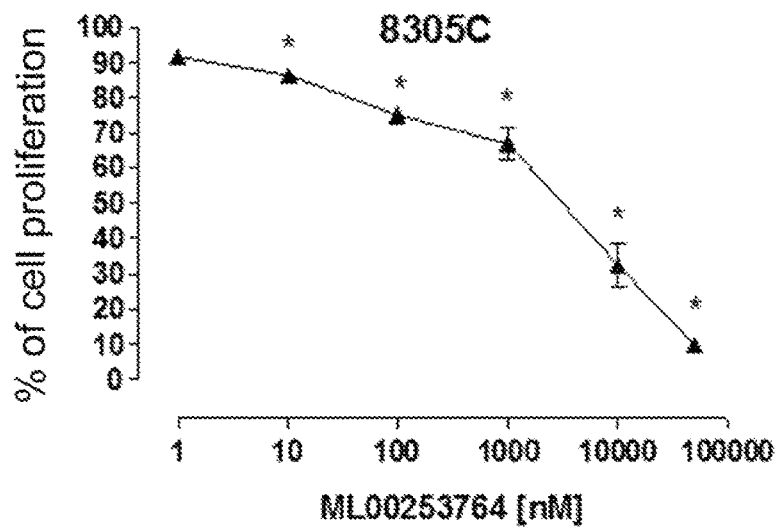
Figure 8:
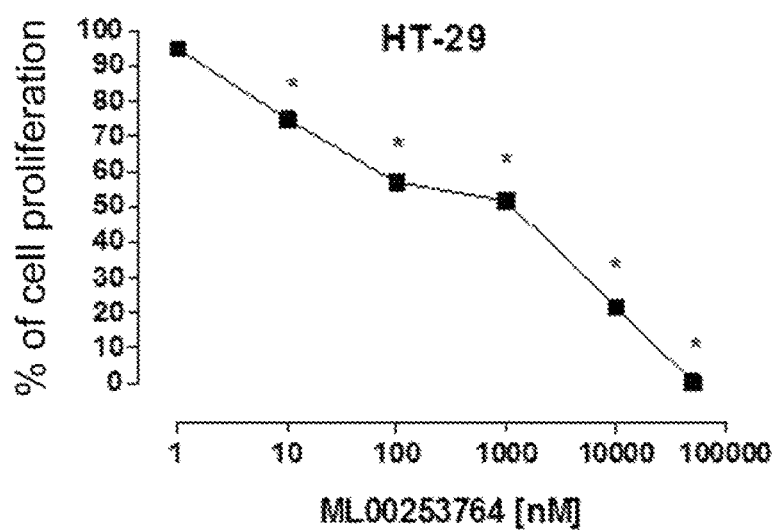
Figure 8:
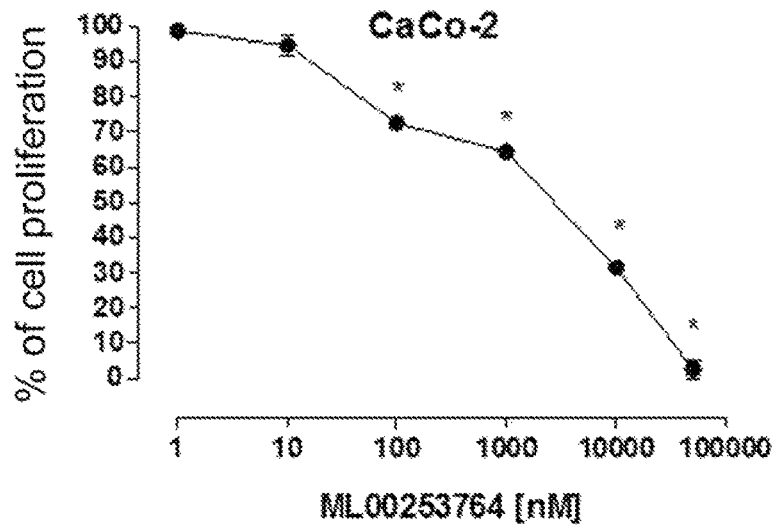

The graphs in FIG. 8 illustrate the in vitro anti-proliferative effect of the melanocortin receptor-4 antagonist ML00253764 on 8305C human thyroid carcinoma cell line (A), and on HT-29 (B) and CaCo-2 (C) human carcinoma cell lines of the gastrointestinal tract. Anti-proliferative effects were studied after 72 hours of drug exposure. The data are presented as mean percentage values (±S.E.M.) of cell proliferation in controls treated with the vehicle alone.

*P<0,0001 vs. controls. All experiments were repeated, independently, three times with at least three samples for each concentration.

Figure 9:
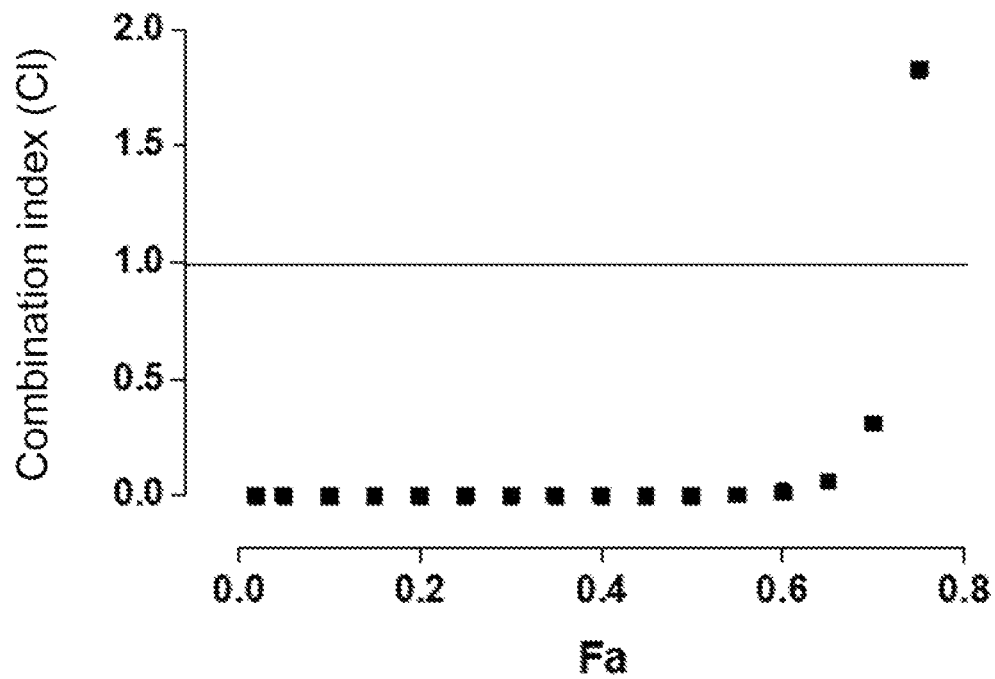
Figure 9:
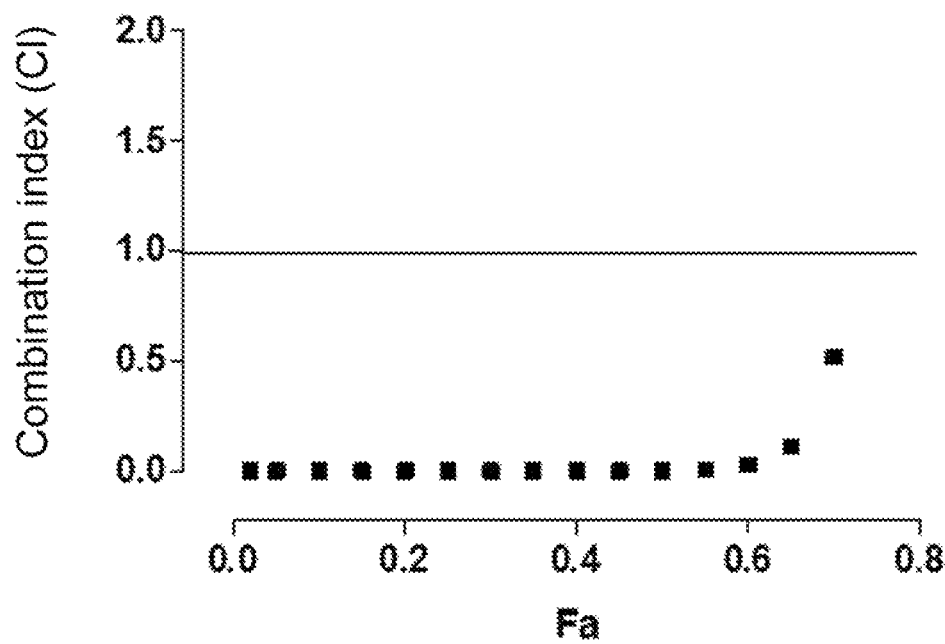

FIG. 9 shows two graphs depicting the Combination Index (CI) curve versus the affected cell fraction (Fa) after simultaneous treatment for 72 hours of A-2058 (A) and WM 266-4 (B) human melanoma cells with the Vemurafenib compound in combination with ML00253764 MC4R antagonist (fixed molar ratio of 1:10). The effect is synergistic for CI values<1 (value represented by the solid horizontal line). The results of the analysis show that the Vemurafenib/ML00253764 combination is highly synergistic.

Figure 10:
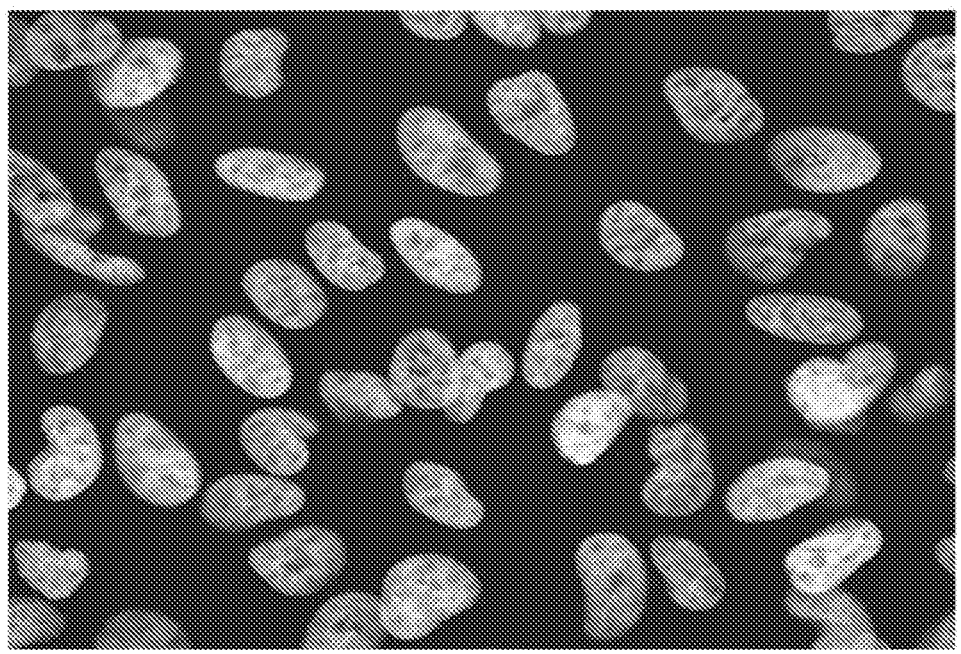
Figure 10:
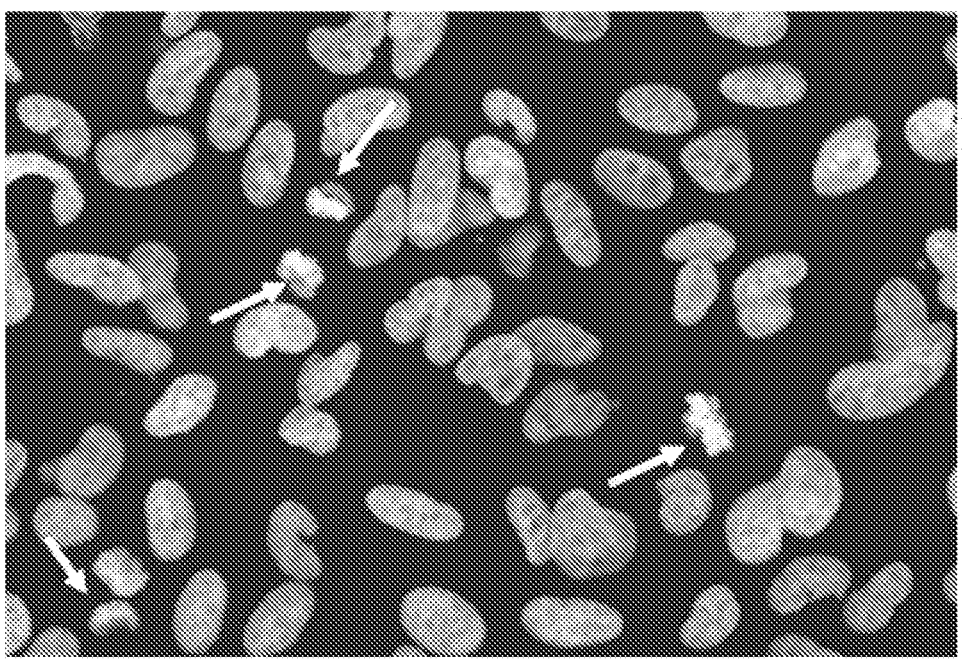

FIG. 10 shows representative photomicrographs of A-2058 human melanoma cells stained with the TO-PRO3 nuclear marker and treated for 72 hours with (A) the vehicle and (B) 10 nM ML00253764. The arrows indicate the increased fluorescence of some "shrunken" nuclei, characteristic of apoptotic cells.

Figure 11:
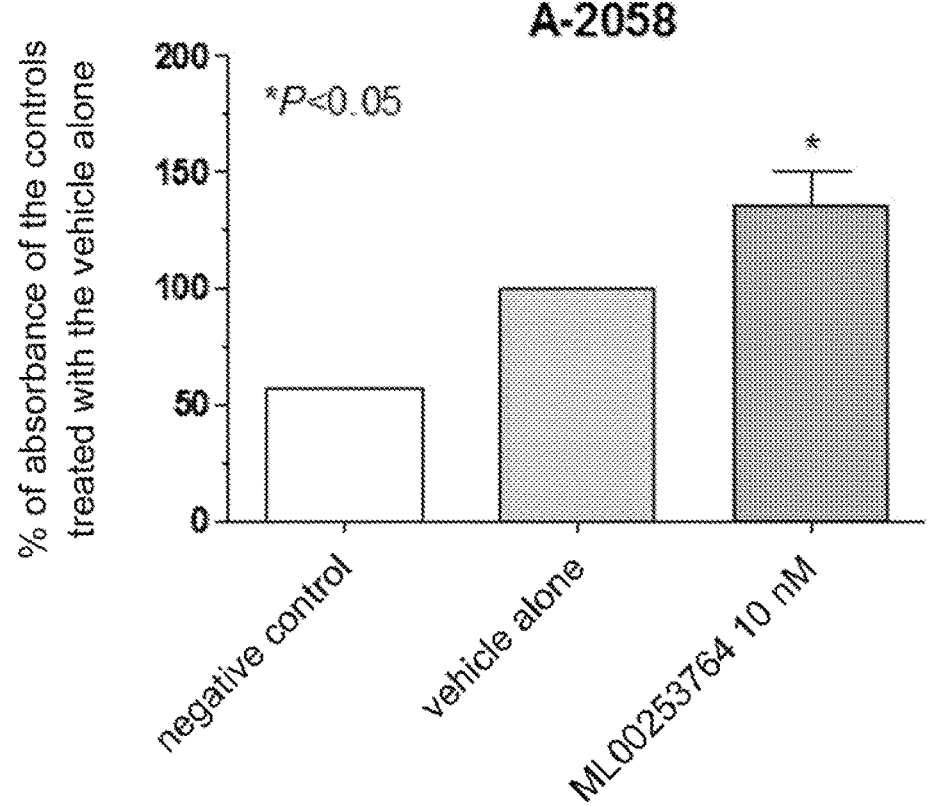
Figure 11:
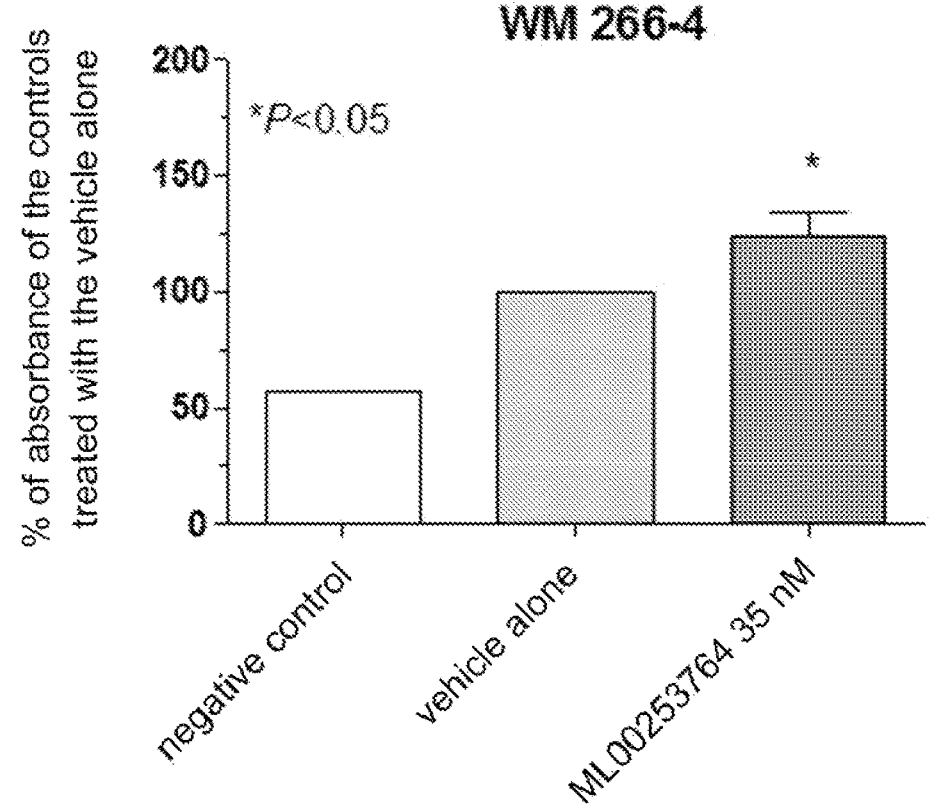

FIG. 11 shows representative histograms of the results from the apoptosis analysis carried out on (A) A-2058 and (B) WM 266-4 human melanoma cells using the "Cell Death Detection ELISA Plus" Kit. The absorbance values shown in the graphs are representative of the cytosolic nucleosomes of cells treated for 72 hours with the vehicle alone or with ML00253764 at the experimental $IC_{50}$s of the respective cell lines. The internal negative control is provided by the kit manufacturer. The data are presented as mean percentage values (±S.E.M.).

Example 1: Cell Lines, Drugs and Reagents

The present study used the human melanoma cell lines A-2058 BRAF-mutant (CRL-11147), obtained from ATCC (American Type Culture Collection, Manassas, USA), and WM-266-4 (91061233), obtained from ECACC (European Collection of Authenticated Cell Cultures). In addition, carcinoma cells of the gastrointestinal tract (Caco-2, HT-29) and thyroid carcinoma cells (8305C) were used. The compound ML00253764 was purchased from Tocris Bioscience (Bristol, UK), and solubilized in sterile water. The compound Vemurafenib was obtained from Selleckchem (Munich, Germany) and dissolved in dimethyl sulfoxide (DMSO). For the in vitro studies, both drugs were dissolved in a stock solution at 10 mM concentration. In the same experiment, the concentration of DMSO in the medium of the controls was the same used to obtain the maximum concentration of Vemurafenib in the cell culture media. The biotinylated anti-rabbit IgG antibody and the avidin-biotin complex were purchased from Vector Laboratories (Burlingame, CA, USA), while TO-PRO-3 iodide was from Molecular Probes (Eugene, OR, USA). Anti-MC4R antibody (ab75506) and goat anti-rabbit IgG antibody (Alexa Fluor 488) were purchased from Abcam (Cambridge, MA, USA).

Example 2: Tumor Cell Culture Conditions

The two tumor cell lines WM-266-4 and A-2058 were grown in cell culture flasks as monolayers and maintained in EMEM and DMEM, respectively, supplemented with 10% fetal bovine serum (FBS), penicillin (50 IU/ml), streptomycin (50 µg/ml) and L-Glutamine (2 mM). The Caco-2, HT-29 and 8305C cells, respectively, were grown in EMEM 20% FBS, McCoy's 5a Medium Modified 10% FBS and RPMI 20% FBS. All reagents used for maintaining tumor cells in culture were purchased from Sigma-Aldrich. The cell lines were maintained in the B5061EK/CO2 mod. Heraeus incubator (Hanau, Germany) at a temperature of 37° C. in a humid atmosphere at 5% CO2. The cells were detached from the culture plates while in the logarithmic growth phase by using a 10× trypsin-EDTA solution and finally plated again to be tested or to keep them in culture.

Example 3: In Vitro Cytotoxicity

For in vitro cytotoxicity studies, WM-266-4 and A-2058 melanoma tumor cells were plated at $1.5 \times 10^4$ cells per well, respectively, in 24-well sterile plates. Twenty-four hours after cell seeding, the culture medium was replaced with fresh medium and the cells were treated with individual drugs. The melanoma cells were treated for 72 hours with the compound ML00253764 in a concentration range of 0.001 µM to 50 µM. As a positive control, the melanoma cells were also individually treated with Vemurafenib, again for 72 hours, in a concentration range of 0.0001 µM to 5 µM. At the end of the experiment the cells were counted by light microscopy in a Burker haemocytometer. The survival of the treated cells was expressed as the mean of the values±S.E.M. from at least 9 wells of the percentage of control cultures (treated with the vehicle alone) and the results were analyzed by non-linear regression. The concentration that reduced cell survival by 50% ($IC_{50}$) compared to controls was finally calculated with GraphPad Prism (version 5.0, San Diego, CA). The simultaneous combination of Vemurafenib and ML00253764 was assessed in the 2 melanoma lines for 72 hours using the aforementioned compounds in a fixed molar ratio of 1:10. The assessment of the level of interaction (synergism, additivity or antagonism) between the compounds ML00253764 and Vemurafenib was performed with the Combination Index (CI) method, according to which CI=1 indicates an additive effect, CI>1 an antagonistic effect and CI<1 a synergistic effect. CI was calculated with the CalcuSyn v.2.0 software (Biosoft, Cambridge, UK).

Following the same procedure as described above, the Caco-2, HT-29 and 8305C cell lines were also tested with the compound ML00253764 for 72 hours, in a concentration range of 0.001 µM to 50 µM. The related $IC_{50}$s were calculated at the end of the experiments.

Example 4: Assessment of Apoptosis by ELISA Test and TO-PRO3

In order to assess the apoptotic activity, the melanoma cells were plated at $2 \times 10^5$ in sterile Petri dishes. The analysis of apoptosis was performed on WM-266-4 and A-2058 cell lines after treatment with the compound ML00253764 at the experimental $IC_{50}$ obtained after 72 hours. After the treatment, the cells were scraped off and recovered with their medium into blind ended tubes and counted in the Burker chamber. An aliquot containing 50,000 cells was centrifuged for 10 minutes at 800 rpm, the pellet thus obtained was lysed with an appropriate volume of lysis buffer for 30 minutes at room temperature, then again centrifuged at 200 g for 10 minutes. The supernatant was used for apoptosis analysis by ELISA assay (Cell Death detection ELISA PLUS, Roche). The ELISA apoptosis assay was performed in 96-well microplates and the absorbance reading was performed by using the Thermo labsystems Multiskan Spectrum reader (M-Medical, MI). To visualize the apoptotic process, $2 \times 10^4$ A-2058 cells were plated on slides in a 12-well plate and treated for 72 hours with the compound ML00253764 at a concentration of 10 nM. At the end of the incubation with the drug, the cells were washed with PBS, fixed and stained with TO-PRO3 iodide. The coverslips were finally mounted, and the slides viewed under a Leica TCS SP5 confocal laser scanning microscope. Apoptosis was confirmed by the characteristic, intensely fluorescent "shrunken" nuclei.

Example 5: MC4R Histochemistry in Melanoma Cells

In order to study the MC4R protein in WM-266-4 and A-2058 cell lines, $2 \times 10^4$ cells were plated on a slide in a 12-well plate. After 72 hours, the cells were fixed in a PBS (pH 7.4) and 4% paraformaldehyde solution for 1 hour at room temperature. The fixed cells were then incubated in a blocking solution consisting of 15% goat serum and 0.2% Triton X-100 in PBS for 30 minutes. The cells were then incubated overnight at 4° C. with the anti-MC4R antibody at a concentration of 20 µg/ml in PBS. The cells were washed with PBS and incubated with the biotinylated anti-rabbit IgG antibody and subsequently with the peroxidase-conjugated avidin-biotin complex. Peroxidase was detected by using diaminobenzidine and hydrogen peroxide. The negative control was performed by omitting the primary antibody. For the immunofluorescence assay, the slides were incubated for 90 minutes with a green-fluorescent goat anti-rabbit secondary antibody diluted 1:250 in PBS. Nuclear staining was performed by incubating the cells with TO-PRO3 diluted 1:1,000 in PBS (pH 7.4) for 15 min. Negative controls were obtained with cells incubated without the primary antibody.

Example 6: MC4R Western Blot Analysis

The lysis buffer (RIPA containing a protease inhibitor mix) was added to the melanoma, gastrointestinal carcinoma and thyroid carcinoma cells, as well as to normal human endothelial cells (HUVEC). After an incubation period of 15 minutes on ice, the cells were sonicated and then centrifuged at 14,000×g for 15 minutes at 4° C. The supernatants were collected, and the protein content was determined. Proteins were denatured, separated by electrophoresis and then blotted onto membranes by using a blotting buffer. The membranes were then blocked, washed and incubated with the primary antibody to MC4R (1:500 dilution) overnight at 4° C. After 24 hours, the membranes were incubated with a specific peroxidase-conjugated secondary antibody (Cell Signaling Technology; Danvers, MA, USA) for 1 hour at room temperature. To verify an equal loading of the wells, β-tubulin expression was analyzed using an anti-β-tubulin antibody. After washing, the membranes were analyzed by chemiluminescence. The bands related to MC4R and β-tubulin (37 and 55 kDa, respectively) were quantified by densitometric scanning through imaging (Bio-Profil, Celbio, Italy). The level of all bands was expressed as the relative integrated intensity normalized to β-tubulin (=100). The data are presented as mean values±S.E.M. for 8-10 repetitions for each cell line.

Example 7: Statistical Analysis

The results of the data obtained herein (mean of the values±S.E.M.) were subjected to statistical analysis by ANOVA followed by Newman-Keuls test or by Student's T-test, using the GraphPad Prism software (version 5.0; GraphPad Prism Software Inc., San Diego, CA, USA). The data significance level was set for P values<0.05.

Figure 1:
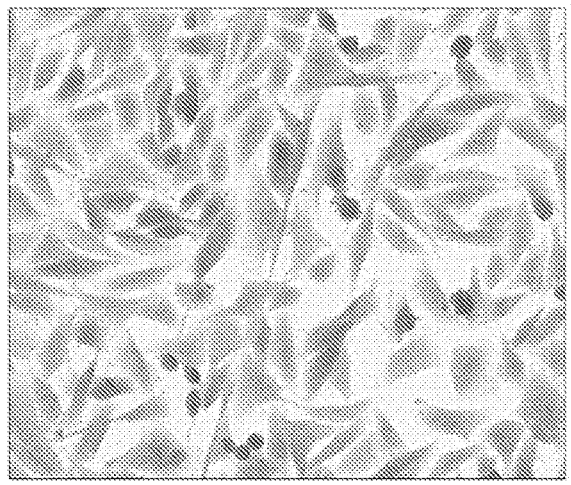
FIG. 1 shows representative photomicrographs of the immunohistochemical analysis performed on (A) anti-MC4R antibody-stained A-2058 human melanoma cells and (B) the respective negative control, without the primary antibody.
Figure 1:
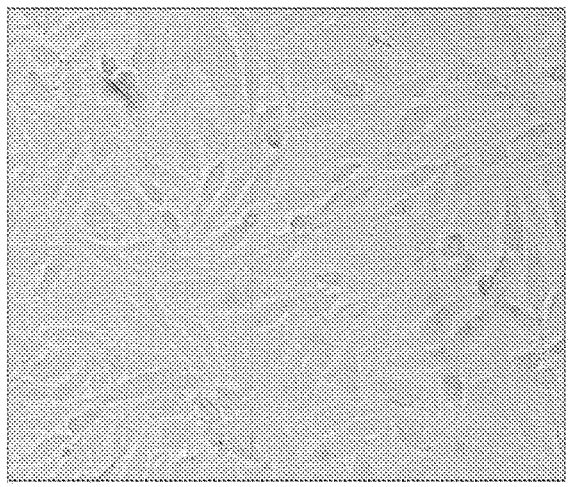
Figure 2:
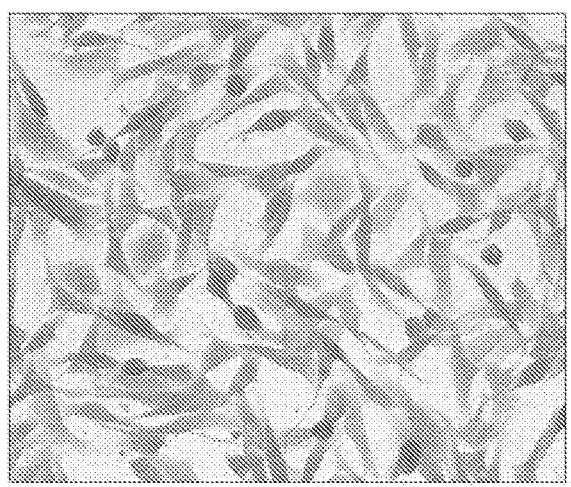
FIG. 2 shows representative photomicrographs of the immunohistochemical analysis performed on (A) anti-MC4R antibody-stained WM 266-4 human melanoma cells and (B) the respective negative control, without the primary antibody.
Figure 2:
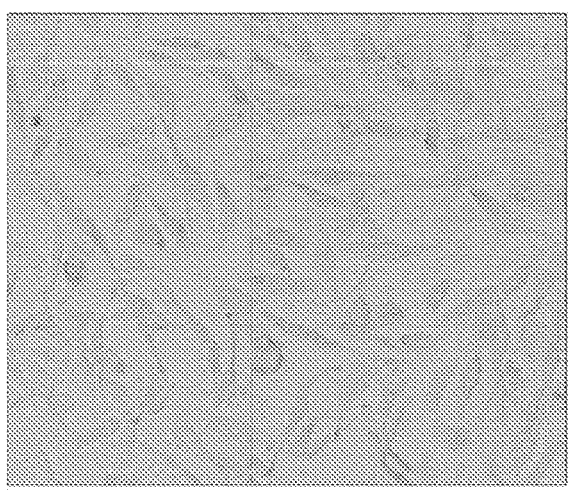
Figure 3:
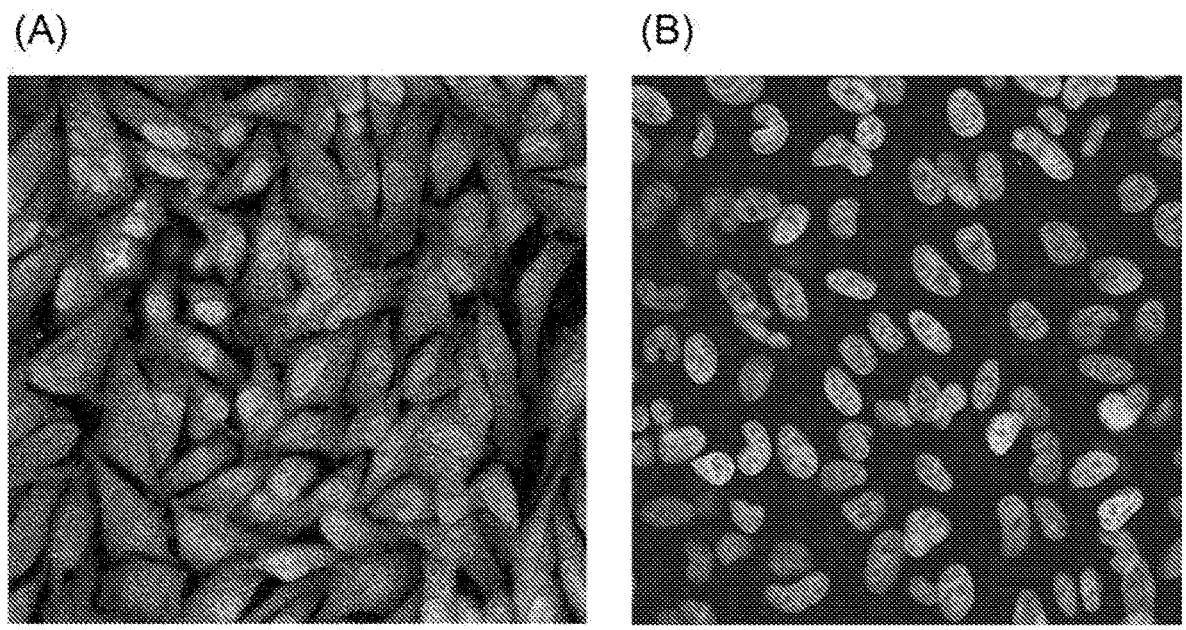
FIG. 3 shows immunofluorescence photomicrographs of (A) anti-MC4R antibody-stained A-2058 human melanoma cells and (B) the respective negative control, without the primary antibody.

Example 8: MC4R Receptor Expression in Melanoma, Gastrointestinal Tumor and Thyroid Carcinoma Cell Lines Immunohistochemical analysis, carried out by the present inventors as shown in Example 5, revealed for the first time that MC4R receptor is significantly expressed in both human melanoma cell lines A-2058 (FIG. 1A) and WM-266-4 (FIG. 2A) when compared to the negative controls in the absence of the primary antibody (FIGS. 1B and 2B). It should be noted that no significant differences were observed between A-2058 and WM-266-4 cells with regard to immunohistochemistry positivity (FIGS. 1 and 2). Furthermore, the immunofluorescence of proliferating cells clearly revealed the presence of the MC4R protein on cell membranes of A-2058 melanoma cells (FIG. 3A), when compared to the negative controls in the absence of the anti-MC4R primary antibody (FIG. 3B).

Figure 4:
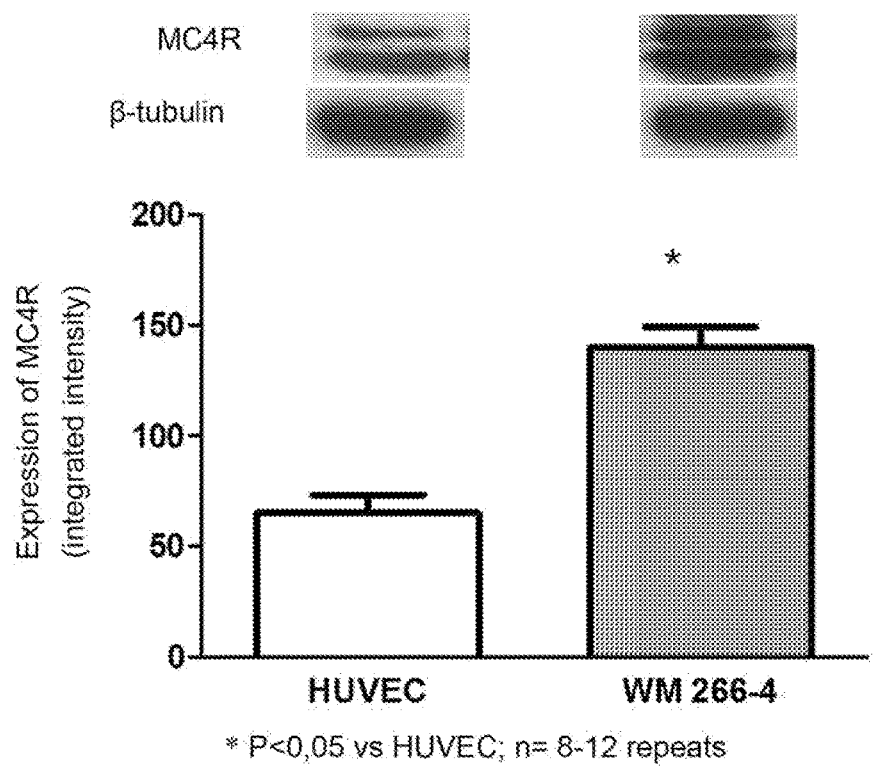
FIG. 4 shows MC4R expression in WM 266-4 human melanoma cell line (right) compared to normal HUVEC endothelial cells (left). Representative photomicrographs of Western blot bands related to MC4R and β-tubulin are shown at the top. A graph showing the results of the imaging of MC4R expression normalized to β-tubulin is shown at the bottom. The data are presented as mean values+S.E.M. for 8-10 repetitions for each cell line. *$P<0.05$ vs. HUVEC cells (Student's t-test). Statistical analyses were performed by using the GraphPad Prism software package version 5.0 (GraphPad Software, Inc., San Diego, CA).

The results of the immunohistochemical analysis were then confirmed by Western blot analysis, which revealed the presence of a high concentration of MC4R protein in human melanoma cells compared to normal HUVEC cells (FIG. 4, top). MC4R levels in human melanoma cells were significantly higher than in endothelial cells in the computerized image analysis of eight to ten repetitions for each cell line (FIG. 4, graph below).

Figure 5:
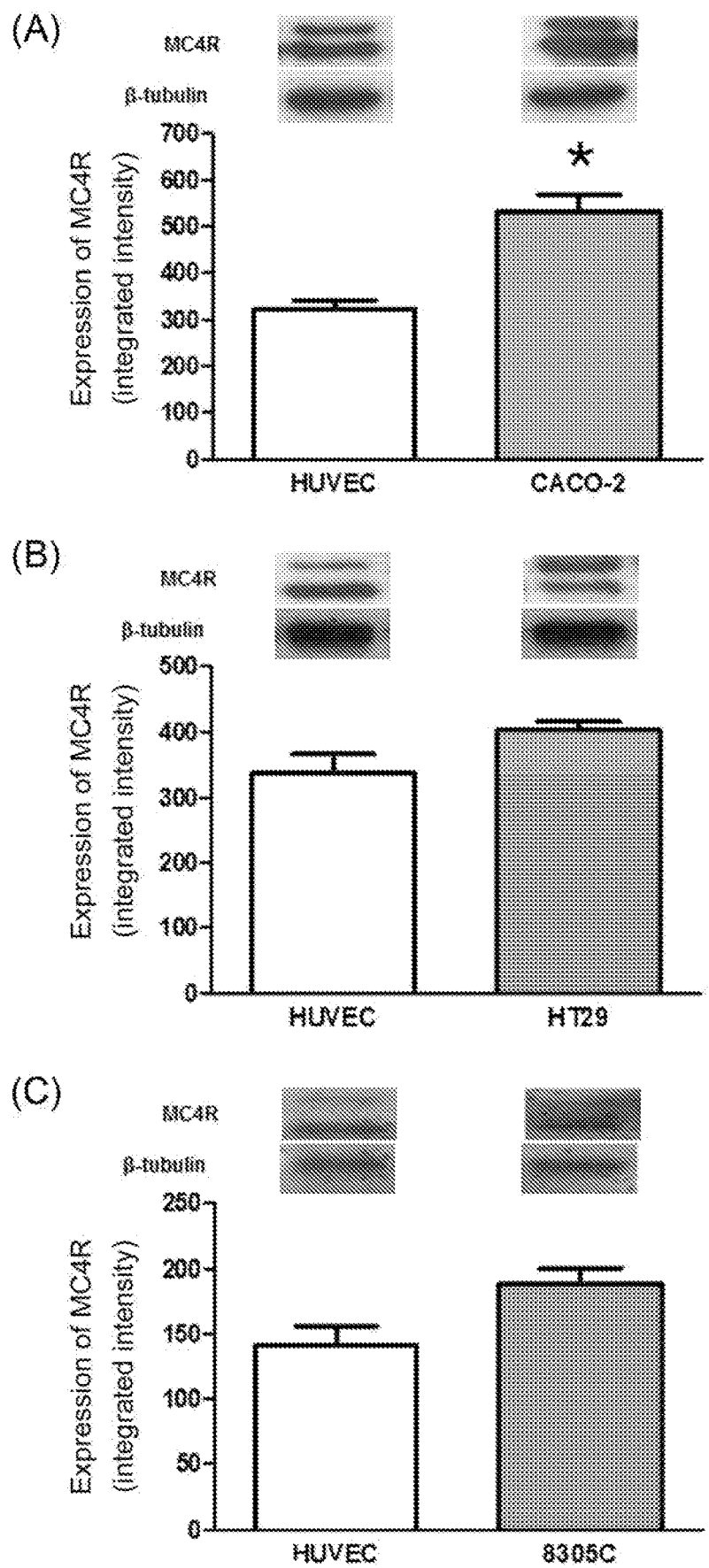
FIG. 5 shows MC4R expression in CaCo-2 (A) and HT-29 (B) human carcinoma cell lines of the gastrointestinal tract, and in 8305C human thyroid carcinoma cell line (C), compared to normal endothelial cells HUVEC. The top of each panel, for each cell line, shows representative photomicrographs of Western bands related to MC4R and β-tubulin. The bottom of each panel shows a graph of the results of the imaging of MC4R expression normalized to β-tubulin. The data are presented as mean values±S.E.M. for 8-10 repetitions for each cell line. *$P<0.05$ vs. HUVEC cells (Student's t-test). Statistical analyses were performed by using the GraphPad Prism software package version 5.0 (GraphPad Software, Inc., San Diego, CA).

By Western blot analysis the present inventors also demonstrated for the first time a significant presence and expression of the MC4R receptor in the Caco-2 (FIG. 5A) and HT-29 (FIG. 5B) gastrointestinal tumor cell lines, as well as in the 8305C thyroid carcinoma cell line (FIG. 5C). A higher concentration of MC4R protein compared to normal HUVEC cells was observed in all cell lines examined (FIGS. 5A, 5B and 5C, top), and MC4R levels in Caco-2, HT-29 and 830C cells were significantly higher than in endothelial cells in the computerized image analysis of eight to ten repetitions (FIGS. 5A, 5B and 5C, graphs below).

Example 9: Antiproliferative Effect of the MC4R Receptor Antagonist on Melanoma, Gastrointestinal Tumor and Thyroid Carcinoma Cells The antiproliferative activity of the MC4R receptor antagonist for use according to the invention was first studied in BRAF-mutant melanoma cell lines. As shown in FIG. 6, the results obtained after 72 hours of treatment with ML00253764 show a significant antiproliferative effect of this compound already at the concentration of 10 nM both in the A-2058 cell line (FIG. 6A) and the WM-266-4 cell line (FIG. 6B) with experimental $IC_{50}$s of 11.1 nM and 33.7 nM, respectively (Table 1). In these studies, the present inventors used as a positive control the compound Vemurafenib, the drug of choice for the treatment of BRAF-mutant melanoma, which is very active in both A-2058 (FIG. 7A) and WM-266-4 (FIG. 7B) cell lines, although with significantly higher $IC_{50}$s (Table 1). In particular, FIG. 7B shows the antiproliferative effects of Vemurafenib on WM-266-4 cells ($IC_{50}$ 46.6 nM, BRAF V600E), whereas the A-2058 cell line shows less sensitivity to the treatment ($IC_{50}$ 526 nM, BRAF V600D), as shown in FIG. 7A.

The present inventors subsequently demonstrated that the MC4R receptor antagonist for use according to the invention is capable of inducing a significant inhibition of the proliferative activity also in the 8305C thyroid carcinoma cell line (FIG. 8A), and the HT-29 (FIG. 8B) and Caco-2 (FIG. 8C) gastrointestinal tumor cell lines. Following treatment with the compound ML00253764 for 72 hours, a significant antiproliferative effect could be seen already at the concentration of 10 nM both in the 8305C cell line (FIG. 8A) and the HT-29 cell line (FIG. 8B) with experimental $IC_{50}$s of 7667 nM and 806.4 nM, respectively (Table 1). The antiproliferative activity of compound ML00253764 in the Caco-2 cell line is shown in FIG. 8C, with an $IC_{50}$ of 2993 nM (Table 1).

Table 1

$IC_{50}$ values of the MC4R antagonist ML00253764 in A-2058 and WM 266-4 human melanoma cell lines, 8305C thyroid carcinoma cell line and HT-29 and Caco-2 gastrointestinal tract tumor cell lines. The drug concentration that reduces cell proliferation by 50% ($IC_{50}$) compared to controls was calculated by interpolating the mean values of the data obtained in triplicate experiments (at least nine wells for each concentration).

|  | IC50 [nM]-72 h | |
| --- | --- | --- |
| Melanoma cell lines | ML00253764 | Vemurafenib |
| A-2058 | 11.1 | 526 |
| WM 266-4 | 33.7 | 46.6 |
| Other cell lines | | |
| 8305C | 7667 | — |
| HT-29 | 806.4 | — |
| CaCo-2 | 2993 | — |

Example 10: Synergistic Therapeutic Effect of the Combination of the MC4R Receptor Antagonist and Vemurafenib In order to verify a potential synergistic effect of the simultaneous treatment by Vemurafenib in combination with the MC4R receptor antagonist for use according to the invention, the present inventors administered these compounds in a fixed 1:10 molar ratio to the two melanoma cell lines. Treatment was carried out for 72 hours. The results of these studies illustrated in the graphs of FIG. 9 show that the simultaneous administration of the combination of ML00253764 and Vemurafenib exerts a marked synergism on the affected cell fractions (Fa) (CI<1) both in A-2058 cells (FIG. 9A) and WM-266-4 cells (FIG. 9B).

Example 11: Pro-Apoptotic Effect of the MC4R Receptor Antagonist for Use According to the Invention By staining with TO-PRO3 iodide nuclear marker, visualized with a confocal laser scanning microscope, the present inventors detected a weak fluorescence of normal-sized nuclei of A-2058 melanoma cells (FIG. 10A) treated with the vehicle alone, indicative of non-apoptotic cells. In contrast, cell samples treated with the compound ML00253764 at a concentration of 10 nM for 72 hours showed an increase in fluorescence with "shrunken" nuclei, characterized by the typical chromatin condensation (FIG. 10B, indicated by arrows), which are peculiar to apoptotic cells. The results of the immunofluorescence assay were confirmed and quantified by using a specific ELISA test. In particular, FIG. 11A shows a significant pro-apoptotic activity of the compound ML00253764 in A-2058 melanoma cells at the concentration of 10 nM (corresponding to the $IC_{50}$) after 72 hours of exposure, whereas using a 35 nM concentration (corresponding to the $IC_{50}$) of this compound induces a significant increase in the apoptotic signal in WM 266-4 cells after 72 hours of exposure (FIG. 11B).

What is claimed is:

1. A method of therapeutic treatment of a tumor pathology selected from the group consisting of melanoma, tumors of the gastrointestinal tract, and thyroid carcinoma, said therapeutic treatment comprising administering to a subject in need thereof a melanocortin receptor-4 antagonist having formula (I)

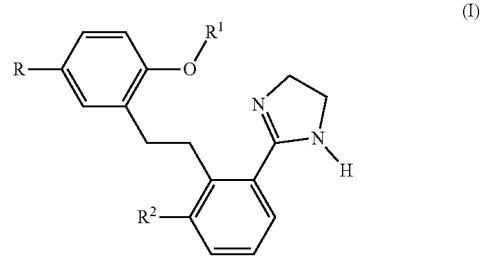

or pharmaceutically acceptable salts and esters thereof, wherein
R and $R^2$ are independently a halogen atom; and
$R^1$ is a $C_1$-$C_4$ alkyl group.

2. The method of claim 1, wherein R is a bromine atom and/or $R^2$ is a fluorine atom.

3. The method of claim 1, wherein $R^1$ is a methyl group.

4. The method of claim 1, wherein the melanocortin receptor-4 antagonist has formula (II)

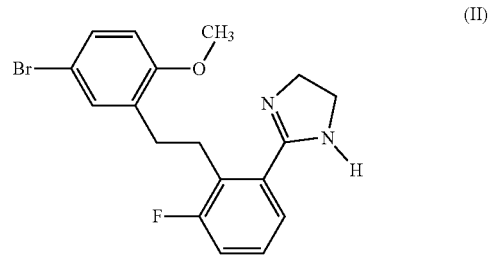 [SMILES: COc1ccc(Br)cc1CCc1c(F)cccc1C1=NCCN1]

5. The method of claim 1, wherein the therapeutic treatment is an adjuvant therapy or a therapy affecting onset and/or progression of metastasis.

6. The method of claim 1, wherein the therapeutic treatment is also suitable for controlling neoplastic cachexia.

7. The method of claim 1, wherein the therapeutic treatment further comprises administering one or more cytotoxic and/or cytostatic agents selected from the group consisting of BRAF inhibitors, MEK inhibitors, tyrosine kinase inhibitors, and combinations thereof.

8. The method of claim 1, wherein the melanocortin receptor-4 antagonist is administered as a pharmaceutical composition, said pharmaceutical composition further comprising at least one pharmaceutically acceptable vehicle, excipient and/or diluent.

9. The method of claim 8, wherein the pharmaceutical composition is in a pharmaceutical form suitable for administered via topical, oral, sublingual, buccal, rectal, subcutaneous, intradermic, transcutaneous, intramuscular, intranasal, inhalation, intravenous, intraarterial, intraperitoneal, intrathecal, intracerebroventricular route or via hyperthermic isolated limb perfusion.

10. The method of claim 9, wherein the pharmaceutical composition is in a pharmaceutical form suitable for being administered to a patient at a daily dose of the melanocortin receptor-4 antagonist comprised between 1 and 100 mg/kg of body weight of the patient.

11. The method of claim 10, wherein the daily dose of the melanocortin receptor-4 antagonist is of at least 50 mg/kg of body weight of the patient.

12. The method of claim 10, wherein the daily dose of the melanocortin receptor-4 antagonist is of at least 25 mg/kg of body weight of the patient.

\* \* \* \* \*